United States Patent [19]

Farber

[11] 4,107,428
[45] Aug. 15, 1978

[54] DI-VINYL COLOR FORMERS

[75] Inventor: Sheldon Farber, Appleton, Wis.

[73] Assignee: NCR Corporation, Dayton, Ohio

[21] Appl. No.: 790,628

[22] Filed: Apr. 25, 1977

Related U.S. Application Data

[63] Continuation-in-part of Ser. No. 566,851, Apr. 10, 1975, Pat. No. 4,020,056.

[51] Int. Cl.² .................. C07D 401/06; C07D 401/14; C07D 403/14
[52] U.S. Cl. ..................................... 542/437; 542/433
[58] Field of Search ............................... 542/433, 437

[56] References Cited

U.S. PATENT DOCUMENTS

| | | | |
|---|---|---|---|
| 3,491,116 | 1/1970 | Lin | 260/326.14 R |
| 3,491,117 | 1/1970 | Lin | 260/326.14 R |
| 3,703,397 | 11/1972 | Lin et al. | 542/420 X |
| 3,736,337 | 5/1973 | Farber | 260/343.3 |
| 3,824,119 | 7/1974 | Terayama et al. | 260/335 X |
| 3,825,561 | 7/1974 | Akamatsu et al. | 260/335 |
| 3,896,116 | 7/1975 | Ozutsumi et al. | 542/401 |
| 3,928,685 | 12/1975 | Alsop | 542/400 X |
| 4,020,056 | 4/1977 | Farber | 260/343.3 R X |
| 4,022,771 | 5/1977 | Farber | 542/441 |
| 4,026,883 | 5/1977 | Farber | 542/441 |

*Primary Examiner*—Winston A. Douglas
*Assistant Examiner*—Thomas A. Waltz
*Attorney, Agent, or Firm*—J. T. Cavender; E. Frank McKinney

[57] ABSTRACT

A chromogenic compound of normally colorless form is disclosed having the following structural formula:

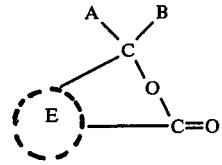

wherein A and B can be

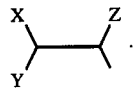

X and Y can be aryl and heterocyclic, each substituted Z is hydrogen and E can be tetrachloro-and tetrabromo-substituted

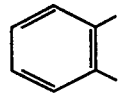

structures. The compound is eligible for use in pressure-sensitive record materials and manifold marking systems. Because of light absorption characteristics, selected compounds of this invention are especially useful where machine readability and machine copiability are important.

7 Claims, 3 Drawing Figures

(I)

(A)

(II)

(B)

(III)

DI-VINYL COLOR FORMERS

This application is a continuation-in-part of copending application Ser. No. 566,851 fild Apr. 10, 1975, issued as U.S. Pat. No. 4,020,056 on Apr. 26, 1977.

BACKGROUND OF THE INVENTION

1. Field of the Invention

This invention pertains to colorable chromogenic compounds eligible for use in pressure-sensitive record material. Pressure-sensitive mark-forming record systems, single sheet and manifold, are improved by use of these compounds.

More specifically, this invention relates to chromogenic compounds having two vinyl linkages which compounds have the form of substantially colorless or slightly colored solids, or which approach being colorless when in liquid solution; but, which may be converted to dark-colored forms upon reactive contact with acidic material. As used in mark-forming systems, marking in desired areas on support webs or sheets may be accomplished by effecting localized reactive contact between the chromogenic material and the acidic material on or in such web or sheet, such material being brought thereto by transfer or originally there, in situ;—the desired reactive contact forming dark-colored materials in the intended image-marking areas.

The chromogenic compounds of this invention have the following general formula:

wherein A and B can be

X and Y can be aryl and heterocyclic, each substituted Z is hydrogen; and E can be tetrachloro- and tetrabromo-substituted structures.

More particularly, the compounds of this invention are represented by the formula:

wherein E is tetrachloro- and tetrabromo-substituted

X is

4—(N— piperidino)phenyl, and 4-(N-pyrrolidino)phenyl; Y is 4-(N-piperidino)phenyl, and 4-(N-pyrrolidino)phenyl; provided when X is Y is and when X is 4-(N-piperidino)phenyl or 4-(N-pyrrolidino)phenyl, Y is the same as X, respectively, or and $R_1$, $R_2$, $R_7$ and $R_8$ are methyl, ethyl, n-propyl or n-butyl groups.

The chromogenic compounds of this invention especially relate to marks at or near the near infrared part of the color spectrum; and, in that regard, especially relate to providing a color which is particularly visible to machine readers and copiers.

2. Description of the Prior Art

Several phthalide and fluoran chromogenic compounds have been disclosed. For example, U.S. Pat. Nos. 3,491,111, and 3,491,116, issued Jan. 20, 1970, disclose indol- and carbazol-substituted phthalides. U.S. Pat. No. 2,417,897, issued Mar. 25, 1947, discloses crystal violet lactone. U.S. Pat. No. 3,681,390, issued Aug. 1, 1972, discloses aryl-substituted fluorans.

U.S. Pat. No. 3,672,935, issued June 27, 1972, discloses use of colorless chromogenic compounds in pressure-sensitive record material.

G. Hallas, in the *Journal of the Society of Dyers and Colourists,* in September, 1967 at pages 368 to 373 and in June, 1970 at pages 237-242 discusses the effects of extended conjugation on colored dye compounds.

SUMMARY OF THE INVENTION

Colorable chromogenic compounds having two vinyl linkages have been discovered which compounds are initially substantially colorless but produce dark-colored products on reaction with certain acid materials. The vinyl-containing chromogenic compounds exhibit light absorption, in the colored form, at wavelengths nearer to infrared than chromogenic compounds without vinyl groups. It is an object of this invention to provide such vinyl-containing compounds and methods for making them.

An important use for the vinyl compounds of this invention resides in their incorporation into pressure-sensitive record systems as a colorable reactant for development of color on application of a mark-forming force. Hence, it is an object of this invention to provide substances having near infrared color response and chromogenic properties, which substances can be incorporated in a web or coated onto the surface of a web to provide a record sheet or manifolding unit, and which are useful in carrying out methods of marking involving reactive contact with a color-activating material to develop dark-colored materials in areas where marking is desired.

It is an object of this invention to provide modified compounds, based upon the aforementioned vinyl-containing compounds, which are substantially colorless, or slightly colored, offering a variety of chromogenic characteristics, and developing dark-colored substances absorbing at increased wavelengths upon contact with color-activating materials.

BRIEF DESCRIPTION OF THE DRAWING

The chromogenic compounds of this invention include a large variety of several moieties, with the vinyl linkages and lactone rings being necessarily common to all. In order to more completely and more distinctly disclose the variety of moiety combinations which forms a part of this invention, a drawing is included which is a schematic representation of the combinations, by structural formula.

Also included as drawings, are graphic representations of the absorption spectra of compounds of this invention compared with the spectra of similar compounds from the prior art.

Figure 1:
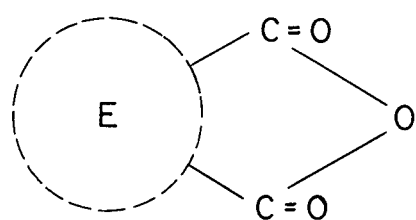
Figure 1:
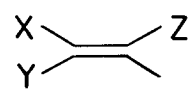
Figure 1:
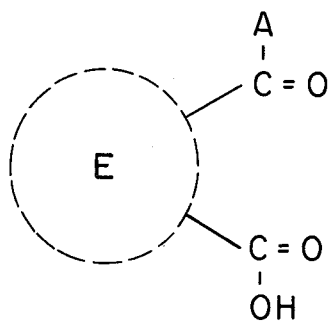
Figure 1:
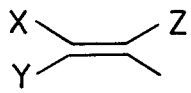
Figure 1:
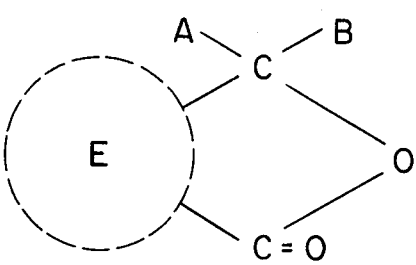

The drawing represents a figurative, schematic, step-by-step structural development of the vinyl-containing compounds of this invention, as they can be prepared. A dicarboxylic anhydride (I) is combined with a vinyl-containing substrate (A) to yield a keto acid (II), which is, in turn, combined with a vinyl-containing substrate reactant (B) to yield the chromogenic compound (III) of this invention. The structural development shown is not necessarily a representation of the actual compound synthesis. For example, in preparing divinyl compounds of this invention, the reaction does not necessarily go through separate and individual steps, as shown; and, in fact, the keto acid (II) may have only a fleeting existence, if it exists at all. The synthetic process is not embraced as a part of this invention.

The dicarboxylic anhydride (I), in FIG. I includes E as the supporting molecular structure. E represents tetrachloro- and tetrabromo- substituted

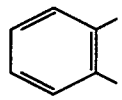

structures. (I) is not required to be a dicarboxylic anhydride. A dicarboxylic acid will suffice if the keto acid-forming reaction is conducted under dehydrating conditions such as in acetic anhydride. Moreover, the vinyl-containing compounds (A) and (B) can be a methyl carbinol under dehydrating conditions.

Figuratively speaking and in accord with the drawing, substrate moieties are added to the supporting molecular structure and the substrate moieties must each contain a vinyl linkage.

(A) and (B) provide structural, schematic, indication of the manner in which vinyl linkages are introduced into the compounds of this invention. While there are differences between the specific moieties which will be disclosed in detail, below, it suffices to say, here, that X and Y represent substituted aromatic and heterocyclic groups and Z represents hydrogen as a part of the moieties of (A) and (B).

Figure 2:
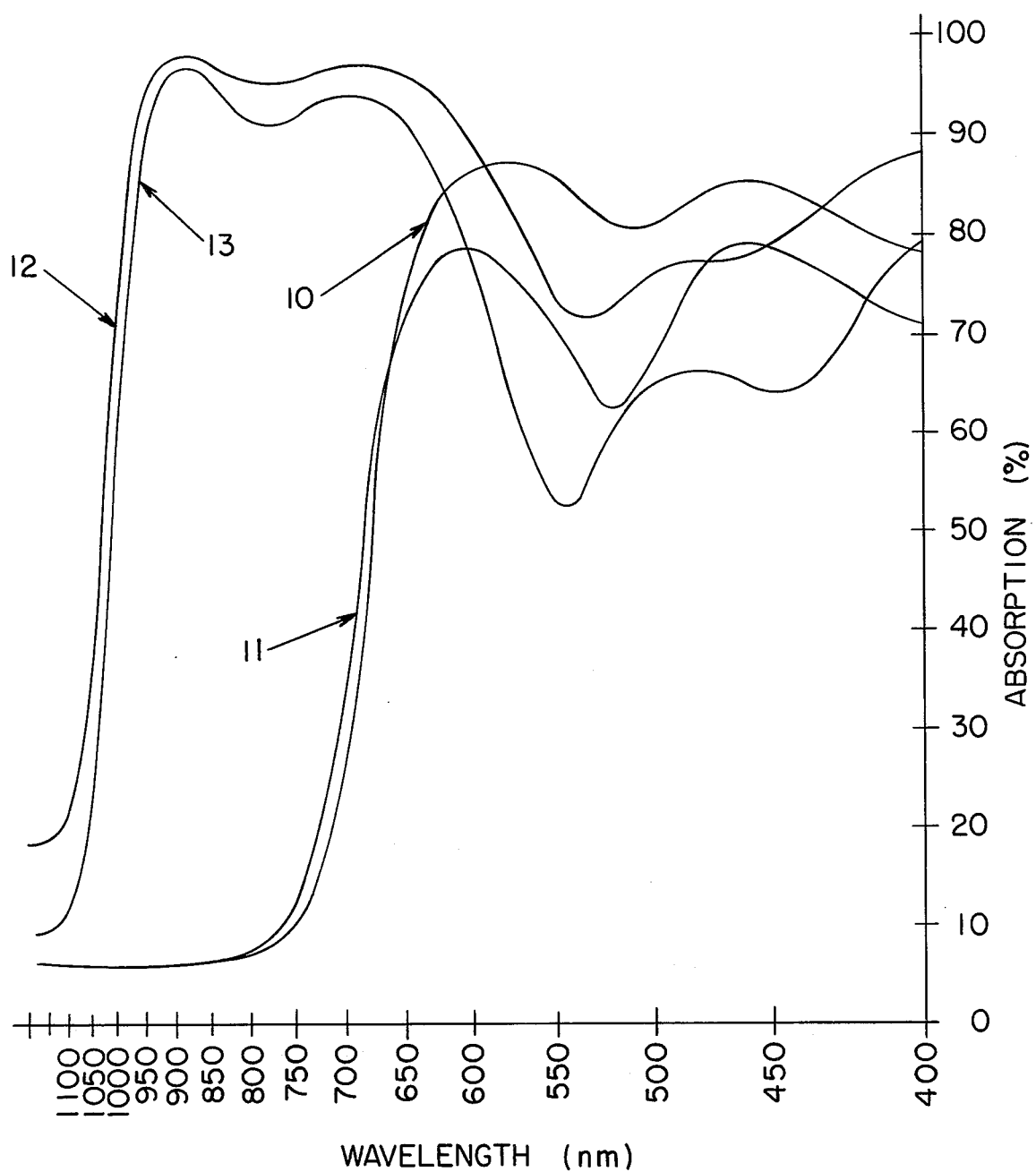
Figure 3:
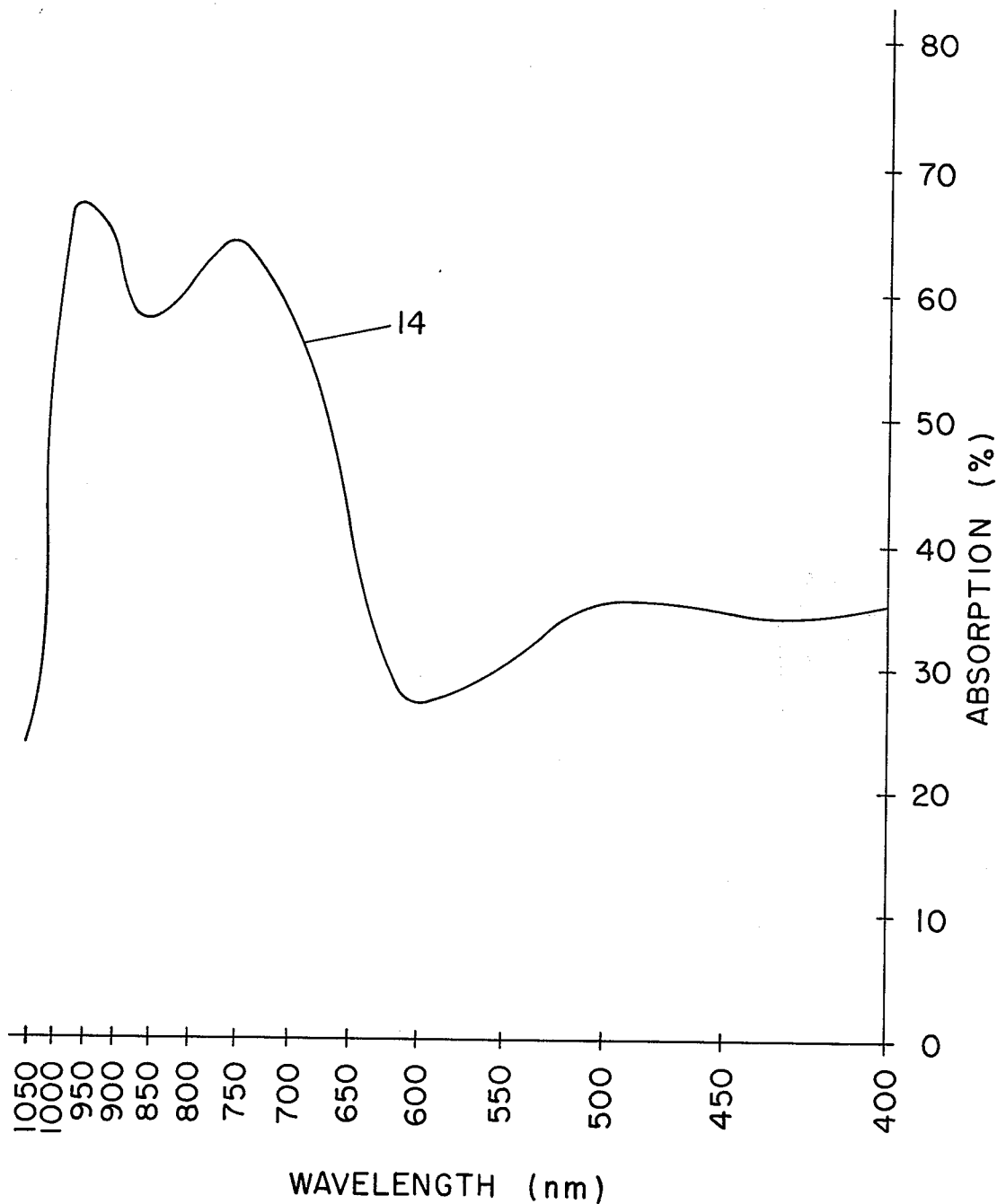

FIG. 2 is a comparative showing of the difference between reflectance of the colored form of the vinyl-containing compounds of this invention and the reflectance of similar compounds, but without the vinyl linkage, from the prior art. FIG. 3 is an additional example of the reflectance of di-vinyl compounds. The abscissa in those graphical showings represents wavelength on a reciprocal scale and the ordinate represents percent of incident light absorbed. Throughout the consideration of this invention, it should be kept in mind that light visible to the human eye exists from about 400 to 700 nanometers wavelength and machine readers and copiers exhibit a maximum sensitivity at about 830 nanometers. FIG. 2 indicates that those compounds of this invention are remarkably more absorbent of light in the machine reading range than are prior art compounds.

The curves of FIGS. 2 and 3 represent the light absorption characteristics of selected chromogenic compounds, in colored form, as reacted from solution on a paper coated with a phenolic resin. In FIG. 2, vinyl color formers of this invention are placed in comparative relation to compounds of the prior art having similar molecular structure or similar visible color; but without the vinyl element.

FIG. 2 is a comparison of the absorption spectra of 2'-anilino-3'-methyl-6'-diethylamino fluoran (10) and 2'-anilino-6'-diethylamino fluoran (11) with the absorption spectra of bis-3,3-[bis-1,1-(p-dimethylaminophenyl)ethyleno-2]-4,5,6,7-tetrachlorophthalide from Example 2, herein, (12) and bis-3,3-[bis-1,1-(p-diethylaminophenyl) ethyleno-2]-4,5,6,7-tetrachlorophthalide from Example 3, herein, (13). The prior art compounds of curves (10) and (11) are not structurally similar to the vinyl-containing compounds of curves (12) and (13); but these prior art compounds have been recognized as among the strongest color reactant absorbers in the wavelength range of about 400 to about 600 nm and higher. The vinyl-containing compounds of curves (12) and (13) are compared thereto as broad wavelength range absorbers.

FIG. 3 is an absorption spectrum of bis-3,3-[bis-1,1-(2-methyl-4-diethylaminophenyl)ethyleno-2]-4,5,6,7-tetrachlorophthalide (14) from Example 2, herein.

The spectral curves (12), (13), and (14) show strong absorption throughout the wavelength range of about 400 to about 1000 nm and especially above about 625 nm.

DETAILED DESCRIPTION OF THE INVENTION

It should be remembered that what is considered to be an essential element of the invention herein is the presence of two vinyl linkages in a colorless but colorable chromogenic material. At the present time, the chromogenic compounds of this invention enjoy extensive eligibility for use in pressure-sensitive and thermally-sensitive mark-forming systems. Pressure-sensitive mark-forming systems provide a marking system of disposing on and/or within sheet support material unreacted mark-forming components and a liquid solvent in which each of the mark-forming components is soluble, said liquid solvent being present in such form that it is maintained isolated by a pressure-rupturable barrier, from at least one of the mark-forming components until application of pressure causes a breach of the barrier in the area delineated by the pressure pattern. The mark-forming components are thereby brought into reactive contact, producing a distinctive mark.

The method of marking comprises providing a chromogenic compound selected from among the above-mentioned compounds and bringing such chromogenic compound into reactive contact, in areas where marking is desired, with an acidic color-activating substance to produce a dark-colored form of the chromogenic compound.

The acidic materials can be any compound within the definition of a Lewis acid, i.e., an electron acceptor. Preferably, acidic organic polymers, such as phenolic polymers, are employed as the acidic material. It is noted that the polymeric mark-forming components should have a common solubility with the chromogenic compound in at least one liquid solvent when the acid-reacting material is a phenolic or other organic acidic polymer. It is also noted that, in a single system, several chromogenic compounds can be used with the same or different polymeric materials. Several polymeric materials can be reactively contacted with a single chromogenic compound or with a mixture of chromogenic compounds.

The acidic polymeric material useful in this invention includes phenol polymers, phenol acetylene polymers, alkyl-phenolacetylene polymers, maleic acid-rosin resins, partially or wholly hydrolyzed styrene-maleic anhydride copolymers and ethylene-maleic anhydride copolymers, carboxy polymethylene and wholly or partially hydrolyzed vinyl methyl ether maleic anhydride copolymers and mixtures thereof.

When the acidic material is one of the aforementioned organic polymers, the liquid solvent chosen must be capable of dissolving the mark-forming components. The solvent can be volatile or non-volatile, and a single or multiple component solvent may be used which is wholly or partially volatile. Examples of volatile solvents useful in the aforedescribed basic chromogen-acidic polymer are toluene, petroleum distillate, perchloroethylene, and xylene. Examples of non-volatile solvents are high-boiling point petroleum fractions, dioctyl adipate, biphenyls, diphenyl alkanes, and the like.

Generally, the solvent chosen should be capable of dissolving at least 0.3 percent, by weight, of chromogenic compounds and at least about 3-5 percent, by weight, of the polymeric material. A further criterion of the solvent is that it must not interfere with the mark-forming reaction.

The support member, on which the components of the system are disposed, may comprise a single or dual sheet assembly. In the case where all components are disposed on a single sheet surface, the record material is referred to as a "self-contained" system. Where there must be a migration of the solvent, with or without mark-forming component, from one sheet to another, the record material is referred to as a "transfer" system. (Such a system can also be referred to as a "two-fold" system, in that at least two sheets are required and each sheet includes a component, or components, essential to the mark-forming reaction.) Where a copious amount of the colored reaction product in liquid form is produced on a surface of one sheet, it can produce a mark by transfer to a second sheet as a colored mark.

The polymeric material can be dissolved in ink composition vehicles to form a printing "ink" of colorless character and, thus, can be used to spot-print a proposed record sheet unit sensitized for recording in a reaction-produced color in those areas by application of a solution of the chromogenic material. In the case of phenolic polymer, a printing ink can be made of up to 75 percent, by weight, of the phenolic polymeric material in a petroleum solvent to a viscosity suitable for printing purposes.

In the mark-forming system herein, the acidic mark-forming component(s) reacts with the chromogenic material(s) to effect distinctive color formation or color change. In a multi-sheet system in which an acid organic polymer is employed, it is desirable to include other materials to supplement the reactants. For example, kaolin can be added to improve the transfer of the liquid and/or the dissolved materials between the sheets. In addition, other materials such as bentonite, attapulgite, talc, feldspar, halloysite, magnesium trisilicate, silica gel, pyrophyllite, zinc sulfide, calcium sulfate, calcium citrate, calcium phosphate, calcium fluoride, barium sulfate and tannic acid can be included. It should be noted that mineral materials such as kaolin, attapulgite, silica gel, silton clay, and the like can, also, be used alone or in combination with other materials as an acidic material coreactant.

Various methods known to the prior art and disclosed in the aforementioned U.S. Pat. No. 3,672,935 can be employed in coating compositions of the mark-forming materials into their supporting sheets. An example of the compositions which can be coated onto the surface of an underlying sheet of a two-sheet system to react with the chromogenic material on the underside of any overlying sheet is as follows:

| Coating Composition | Percent by Weight |
| --- | --- |
| Phenolic polymer mixture | 17 |
| Paper coating kaolin (white) | 57 |
| Calcium carbonate | 12 |
| Styrene butadiene latex | 4 |
| Ethylated starch | 8 |
| Gum arabic | 2 |
|  | 100 |

Thermally-sensitive mark-forming systems can also be prepared using the compounds of this invention.

The compounds of this invention can be prepared to be symmetrical as will be discussed in the examples which follow. Referring, again, to FIG. 1;—E can be tetrachloro- and tetrabromo-substituted:

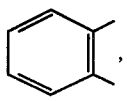

X can be

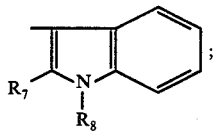

4-(N-piperidino)phenyl, having the formula,

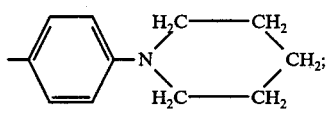

and 4-(N-pyrrolidino)-phenyl having the formula,

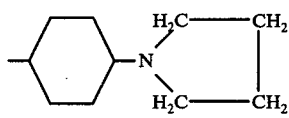

Y can be

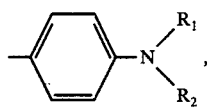

4-(N-piperidino)-phenyl, and 4-(N-pyrrolidino)phenyl; provided when X is

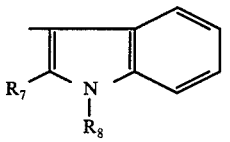

Y is

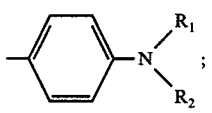

and when X is 4-(N-piperidino)phenyl or 4-(N-pyrrolidino)phenyl, Y is the same as X, respectively, or

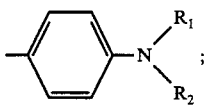

wherein $R_1$, $R_2$, $R_7$ and $R_8$ are alkyl.

Y can be any X and hydrogen.

Z can be hydrogen.

It should be understood that "alkyl" means methyl, ethyl, n-propyl and n-butyl.

This invention is further illustrated by the following examples. The reactants and the proportions and other specific conditions are represented as being typical and should not be construed to limit the invention.

DESCRIPTION OF THE PREFERRED EMBODIMENTS

In the following examples, general procedures for preparing certain compounds of this invention are disclosed; and the procedures are followed by summaries of additional compounds prepared in similar manner. The summaries are not intended to be exhaustive and it must be remembered that the moieties, as previously defined, are all eligible for use in any combination in preparing the compounds.

EXAMPLE 1

Preparation of bis-3,3-[bis-1,1-(p-dimethylaminophenyl) ethyleno-2]phthalide.

With reference to the drawing in respect of this example and like examples which follow, the description of compound preparation does not specifically proceed through the keto-acid (II) although the keto-acid intermediate is exhibited in the drawing.

For ease in understanding, the Examples are summarized in listings of components: the (I) component, generally anhydride, and the (A) and (B) ethylene substrate components. The summarized listing of exemplary eligible compounds is believed to facilitate understanding of the invention.

Combining an appropriate anhydride with an appropriate ethylene base, results in a compound of this invention. This example will be given with details of reaction conditions and will be followed by an additional listing of exemplary compounds.

A mixture of 1.4 grams of phthalic anhydride (I) and 13.4 grams of bis-1,1-(p-dimethylaminophenyl)ethylene (A and B) is heated to reflux in 25 milliliters of acetic anhydride. The system is poured into ice and ammonia and extracted with toluene and the toluene is dried with sodium sulfate. The reaction product is recrystallized from heptane and toluene-petroleum ether and then is chromatographed. The product imparts a green color to paper coated with a phenolic resin or silton clay or a combination of the two. A reflectance spectrum of the green color has a peak at 850 nanometers.

Example 1, Summarized (I) phthalic anhydride
(A), (B) bis-1,1-(p-dimethylaminophenyl)ethylene
green. absorption peak at 850 nanometers
also (A), (B) bis-1,1-(p-diethylaminophenyl)ethylene

EXAMPLE 2

Preparation of bis-3,3-[bis-1,1-(p-dimethylaminophenyl)ethyleno-2]-4,5,6,7-tetrachlorophthalide A mixture of 28.6 grams of tetrachloro-phthalic anhydride and 51.3 grams of 1,1-bis-(p-dimethylaminophenyl)ethylene are heated in 400 milliliters of acetic anhydride, at about 74° C, for about one hour. The system is slowly cooled and the reaction product is filtered from the system and then dissolved in about 1200 milliliters of hot toluene. That toluene solution is cooled and 700 milliliters of petroleum ether is added. After standing for about 12 hours, 56.5 grams of reaction product is separated by filtration and that reaction product exhibits a melting point of 247°–249° C. A solution of the product imparts a dark green color to paper coated with a phenolic resin or silton clay or a combination of the two. A reflectance spectrum of the green color has peaks at 690 and 880 nanometers. The calculated analysis for $C_{44}H_{42}N_4O_2Cl_4$, the title compound, is C, 66.33%; H, 5.31%; N, 6.54%; and Cl, 17.80%. Found, on analysis: C, 66.53%; H, 5.45%; N, 6.79%; and Cl, 17.46%.

With the anhydrides of this Example bromine can be used rather than chlorine. It is understood, of course, that for different reactant component materials, the weight amounts must be adjusted to provide about one mol of (A) and (B) for each mol of (I).

Example 2, Summarized (I) 3,4,5,6-tetrachloro phthalic anhydride
(A), (B) bis-1,1-(p-dimethylaminophenyl)ethylene green. absorption peaks at 690 and 880 nanometers
(A), (B) bis-1,1-(2-methyl-4-dimethylaminophenyl)ethylene neutral. absorption peak at 950 nanometers
(A), (B) bis-1,1-(2-methyl-4-diethylaminophenyl)ethylene neutral. absorption peaks at 925 and 740 nanometers
also (A), (B) bis-1,1-(2-ethoxy-4-deimethylaminophenyl)ethylene
also (A), (B) bis-1,1-(2-dimethylamino-4-diethylaminophenyl)ethylene
(I) 3,4,5,6-tetrabromophthalic anhydride
(A), (B) bis-1,1-(p-dimethylaminophenyl)ethylene

EXAMPLE 3

3,4,5,6-tetrachlorophthalic anhydride (1 mol part) is mixed with bis-(1,1-p-diethylaminophenyl)methylcarbinol (2 mol parts) in acetic anhydride and reacted as previously disclosed. The reaction product is bis-3,3-[bis-1,1-(p-diethylaminophenyl)ethyleno-2]-4,5,6,7-tetrachlorophthalide. The calculated analysis for $C_{50}H_{58}N_4O_2Cl_4$, the reaction product, is C, 68.43%; H, 6.40%; N, 6.14%; and Cl, 15.15%. Found, on analysis: C, 68.59%; H, 6.37%; N, 6.03%; and Cl, 15.38%. A solution of the material imparts a deep green color to paper coated with phenolic resin or silton clay or a combination of the two. A reflectance spectrum of the green color has peaks at 690 and 880 nanometers.

EXAMPLE 4

Preparation of bis-3,3-[bis-1,1-(p-dimethylaminophenyl) ethyleno-2]-4(or 7)-nitrophthalide.

A mixture of 1.93 grams of 3-nitrophthalic anhydride and 5.3 grams of bis-1,1-(p-dimethylaminophenyl)ethylene is refluxed and reacted by the procedures previously disclosed; and the reaction product is isolated, as previously disclosed. The reaction product has a melting point of 208°–210° C. A solution of the product imparts a deep green color to a paper coated with phenolic resin or silton clay or a combination of the two. A reflectance spectrum of the green color has absorption peaks at about 660 and 880 nanometers.

Example 4, Summarized (I) 3-nitrophthalic anhydride
(A), (B) bis-1,1-(p-dimethylaminophenyl)ethylene green. absorption peaks at 660 and 880 nanometers

EXAMPLE 5

Preparation of bis-3,3-[1-(p-dimethylaminophenyl)-1-(1-ethyl-2-methylindol-3-yl)ethylene]-4,5,6,7-tetrachlorophthalide.

To 5 milliliters of acetic anhydride heated to 94° C is added 3.1 grams of 1-(p-dimethylaminophenyl)-1-(1-ethyl-2-methylindol-3-yl)ethylene and 1.4 grams of tetrachlorophthalic anhydride. After 15 minutes the reaction mixture is cooled and filtered. The filtered material is washed three times with one milliliter portions of acetic anhydride. The material is recrystallized three times from toluene-petroleum ether. The purified material exhibits a melting point of 264°–264.5° C. A solution of the product imparts a green-blue color to paper coated with a phenolic resin. A reflectance spectrum of the green-blue color has an absorption peak at 860 nanometers. The calculated analysis for $C_{50}H_{46}N_4O_2Cl_4$, the title compound, is C, 68.49%; H, 5.29%; N, 6.39%; and Cl, 16.18%. Found, on analysis: C, 68.61%; H, 5.32%; N, 6.21%; and Cl, 16.14%.

Example 5, Summarized (I) 3,4,5,6-tetrachlorophthalic anhydride
(A), (B) 1-(p-dimethylaminophenyl)-1-(1-ethyl-2-methylindol-3-yl)ethylene, green-blue, absorption peak at 860 nanometers.
(I) 3,4,5,6-tetrabromophthalic anhydride
(A), (B) 1-(p-dimethylaminophenyl)-1-(1-ethyl-2-methylindol-3-yl)ethylene, green, absorption peak at 833 nanometers.

EXAMPLE 6

Preparation of bis-3,3-[1-(p-dimethylaminophenyl)-1-(p-Piperidinophenyl)ethylene]-4,5,6,7-tetrachlorophthalide.

A mixture of 3.5 grams of 1-(p-dimethylaminophenyl)-1-(p-piperidinophenyl)ethanol, 1.4 grams of tetrachlorophthalic anhydride and 10 milliliters of acetic anhydride is heated at 95° C for 20 minutes. The reaction mixture is cooled, diluted with toluene and ammonia added with cooling. The toluene layer is separated, washed with water and dried by passing through phase separating paper. The toluene solution is concentrated to produce a solid residue. The residue is washed with petroleum ether, dissolved in toluene, petroleum ether added to the toluene solution and the solution is filtered. Additional petroleum ether is added to the solution to promote crystallization of the product. The resulting crystallized product is recrystallized four times producing a material which melts at 132° C. The product produces a single spot during silica gel thin layer chromatography. C-13 NMR shows the material to be a mixture of cis and trans isomers. A solution of the product imparts a green color on both paper coated with phenolic resin and paper coated with silton clay. A reflectance spectrum of the green color has an absorption peak at 884 nanometers.

Example 6, Summarized (I) 3,4,5,6-tetrachlorophthalic anhydride
(A), (B) 1-(p-dimethylaminophenyl)-1-(p-piperidinophenyl) ethylene, green, absorption peak at 884 nanometers.
(A), (B) bis-1,1-(p-piperidinophenyl)ethylene, green, absorption peak at 893 nanometers.
also (I) 3,4,5,6-tetrachlorophthalic anhydride (A), (B) 1-(p-dimethylaminophenyl)-1-(p-pyrrolidinophenyl)ethylene
(A), (B) bis-1,1-(p-pyrrolidinophenyl)ethylene
(I) 3,4,5,6-tetrabromophthalic anhydride
(A), (B) 1-(p-dimethylaminophenyl)-1-(p-piperidinophenyl) ethylene, green, absorption peak at 893 nanometers.
(A), (B) bis-1,1-(p-piperidinophenyl)ethylene, green, absorption peak at 893 namometers.

What is claimed is:

1. A compound represented by the formula:

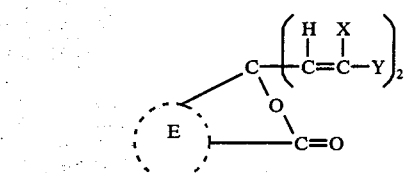

wherein E is tetrachloro- and tetrabromo-substituted

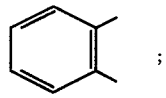

X is

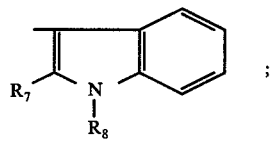

4-(N-piperidino)phenyl, and 4-(N-pyrrolidino)phenyl; Y is

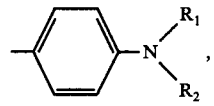

4-(N-piperidino)phenyl, and 4-(N-pyrrolidino)phenyl; provided when X is

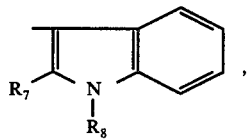

Y is

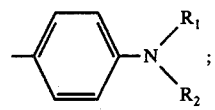

and when X is 4-(N-piperidino)phenyl or 4-(N-pyrrolidino)phenyl; Y is the same as X, respectively, or

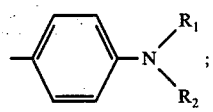

and $R_1$, $R_2$, $R_7$ and $R_8$ are methyl, ethyl, N, propyl or N-butyl groups.

2. The compound of claim 1 wherein X is

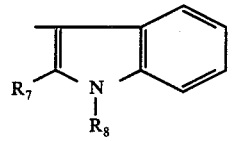

and Y is

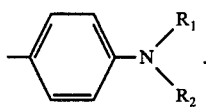

3. The compound of claim 2 wherein $R_1$ and $R_2$ are methyl.

4. The compound of claim 3 wherein E is tetrachloro-substituted

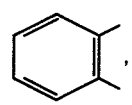

$R_7$ is ethyl and $R_8$ is methyl.

5. The compound of claim 1 wherein X and Y are 4-(N-piperidino) phenyl.

6. The compound of claim 1 wherein X is 4-(N-piperidino)phenyl and Y is

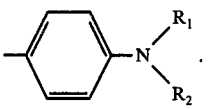

7. The compound of claim 6 wherein $R_1$ and $R_2$ are methyl.

* * * * *